United States Patent [19]

Spivak et al.

[11] Patent Number: 4,611,023
[45] Date of Patent: Sep. 9, 1986

[54] DI-(SUBSTITUTED HYDROXYPHENYLTHIO) ALKANE AND CYCLOALKANE STABILIZERS AND STABILIZED COMPOSITIONS

[75] Inventors: John D. Spivak; Stephen D. Pastor, both of Spring Valley, N.Y.

[73] Assignee: Ciba-Geigy Corporation, Ardsley, N.Y.

[21] Appl. No.: 756,147

[22] Filed: Jul. 17, 1985

Related U.S. Application Data

[63] Continuation of Ser. No. 576,691, Feb. 3, 1984, abandoned.

[51] Int. Cl.$^4$ .................. C07C 149/36; C08K 5/37
[52] U.S. Cl. .................. 524/326; 524/331; 568/47
[58] Field of Search .................. 568/47; 524/331, 326; 252/48.2

[56] References Cited

U.S. PATENT DOCUMENTS

| | | | |
|---|---|---|---|
| 2,883,365 | 4/1959 | Mathes | 524/326 |
| 2,894,004 | 7/1959 | Dietzler | 524/326 |
| 3,489,804 | 1/1970 | O'Shea | 524/331 |
| 3,576,883 | 4/1971 | Neuworth | 568/47 |
| 3,704,327 | 11/1972 | Neuworth | 568/47 |
| 3,751,483 | 8/1973 | Cisney | 524/331 |
| 3,786,100 | 1/1974 | Neuworth | 568/47 |
| 3,897,500 | 7/1975 | Neuworth | 568/47 |
| 3,956,359 | 5/1976 | Neuworth | 568/47 |
| 4,108,831 | 8/1978 | Cottman | 568/47 |
| 4,128,530 | 12/1978 | Cottman | 524/330 |
| 4,330,462 | 5/1982 | Keck et al. | 524/331 |

FOREIGN PATENT DOCUMENTS 42-14532 8/1967 Japan .
1148550 12/1967 United Kingdom .

OTHER PUBLICATIONS

Index Chemicus 28, 92737(1968).
CA 67, 1067 (1967).
M. B. Neuworth et al., J. Medicinal Chem. 13, 722 (1970).
CA 93, 71280x (1980).
CA 93, 94980q (1980).
CA 93, 149970u (1980).

Primary Examiner—Veronica P. Hoke
Attorney, Agent, or Firm—Luther A. R. Hall

[57] ABSTRACT

Organic materials are stabilized against thermal, oxidative and photo-degradation by incorporating therein an effective amount of a compound of formula I

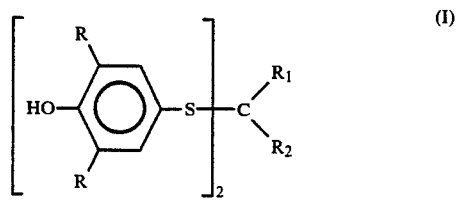

wherein R is tert-butyl, $R_1$ is hydrogen or alkyl of 1 to 4 carbon atoms, $R_2$ is alkyl of 1 to 17 carbon atoms, cyclohexyl, cyclohex-3-enyl, phenyl or 3,5-di-tert-butyl-4-hydroxyphenyl; where $R_1$ and $R_2$ together must have a total of at least 5 carbon atoms; or where $R_1$ and $R_2$ together are alkylene of 5 to 11 carbon atoms. Polyolefins, ABS resins, natural and synthetic rubbers and polyesters are particularly well stabilized by the compounds of formula I.

10 Claims, No Drawings

DI-(SUBSTITUTED HYDROXYPHENYLTHIO) ALKANE AND CYCLOALKANE STABILIZERS AND STABILIZED COMPOSITIONS

This is a continuation of application Ser. No. 576,691, filed on Feb. 3, 1984, now abandoned.

The present invention pertains to alkane or cycloalkane moieties containing two substituted hydroxyphenylthio groups which are useful as stabilizers for organic materials and to stabilized compositions containing said compounds.

BACKGROUND OF THE INVENTION

Organic polymeric materials such as plastics, rubber and resins, and synthetic, lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered. These and other undesirable degradative effects may originate as a result of thermal degradation, oxidation, photodegradation or some combination of these processes with the organic materials under conditions which are not well understood.

It has now been determined that the compounds of this invention possess an unusual combination of desirable properties which makes them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of crosslinking, crazing, discoloration, odor formation and exudation are basic requirements.

Some of the hydroxyphenylthio compounds found useful in stabilizing organic substates are known.

A related series of U.S. Pat. Nos. 3,576,883; 3,786,100; 3,897,500 and 3,956,359 disclose keto substituted alkylidenedithiobisphenols wherein bis(3,4-di-tert-butyl-4-hydrophenyl) groups and various alkylidene bridging groups are present. In all cases a methyl substituent must appear on the alkylidene linking member of these compounds. The compounds of these patents are found useful for reducing blood cholesterol levels in warm-blooded animals and no mention or suggestion of their possible use as stabilizers is made.

M. B. Neuworth et al., J. Medicinal Chemistry, 13, 722 (1970) describes the same compounds as disclosed in the four patents mentioned supra as well as a number of comparable alkylidenedithiophenols having a variety of substituent groups on the phenyl ring and on the linking alkylidene member. Again, the only utility given for said compounds is for hypocholesterolemic activity in warm-blooded animals.

Three Japanese Kokai Nos. 79/163,536; 80/9,041 and 80/17,316 (CA, 93, 71280x (1980); CA, 93, 94980q (1980) and CA, 93, 149970u (1980) respectively) describe 2,2-bis(3,5-di-tert-butyl-4-hydroxyphenylthio)-propane as a hypocholesterolemic agent.

U.S. Pat. No. 3,704,327 discloses bis(3-methyl-5-tert-butyl-4 hydroxyphenylthio)methane and 1,1-bis(3-methyl-5-tert-butyl-4-hydroxyphenylthio)ethane as antioxidants for rubber. The instant compounds differ structurally from these prior art compounds by being substituted on the phenyl ring by two tert-butyl groups ortho to the hydroxy in each ring and by having the alkylidene linking member substituted by a total of at least five carbon atoms. The instant compounds provide better stabilization performance in a variety of substrates than do the two prior art compounds of U.S. 3,704,327.

OBJECTS OF THE INVENTION

It is the primary object of this invention to provide a class of hydroxyphenylthio compounds which exhibit a broad range of improved stabilization performance characteristics.

It is a further object to provide a group of novel compounds within the above-noted class.

DETAILED DISCLOSURE

The instant invention pertains to organic materials stabilized against the deleterious effects of thermal, oxidative and photo-degradation by the incorporation therein of an effective amount of a compound of formula I

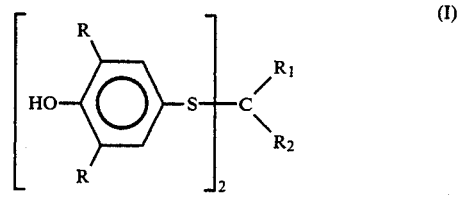

wherein
R is tert-butyl,
$R_1$ is hydrogen or a straight- or branched-chain alkyl of 1 to 4 carbon atoms,
$R_2$ is a straight- or branched-chain alkyl of 1 to 17 carbon atoms, cyclohexyl, cyclohex-3-enyl, phenyl or 3,5-di-tert-butyl-4-hydroxyphenyl; where $R_1$ and $R_2$ together must have a total of at least 5 carbon atoms; or
$R_1$ and $R_2$ together are alkylene of 5 to 11 carbon atoms.

When $R_1$ is a straight- or branched-chain alkyl of 1 to 4 carbon atoms, $R_1$ is, for example, methyl, ethyl, isopropyl, n-propyl, isobutyl and the like.

When $R_2$ is a straight- or branched-chain alkyl of 1 to 17 carbon atoms, $R_2$ is, for example, methyl, ethyl, isopropyl, isobutyl, n-hexyl, 2,4-dimethylamyl, 3-heptyl, n-nonyl, n-undecyl, n-heptadecyl and the like.

When $R_1$ and $R_2$ together are alkylene of 5 to 11 carbon atoms, they are, for example, pentamethylene, hexamethylene, heptamethylene or undecamethylene and the like.

Preferably $R_1$ is hydrogen or methyl.

When $R_2$ is alkyl, $R_2$ is preferably alkyl of 6 to 8 carbon atoms.

When $R_1$ and $R_2$ together are alkylene, $R_1$ and $R_2$ together are preferably pentamethylene.

The stabilizer compounds are prepared by reacting the appropriate 4-mercaptophenol with the appropriate carbonyl compound in the presence of a strong acid catalyst, such as hydrogen chloride. The reaction is preferably conducted in an inert organic solvent, such as methanol, heptane, benzene or toluene. The reaction temperature generally ranges from 0° to 100° C. The starting materials are generally items of commerce or can be prepared by known methods.

Compounds of this invention are particularly effective in stabilizing organic materials such as plastics, polymers and resins in addition to mineral and synthetic fluids such as lubricating oils, circulating oils, etc.

Substrates in which the compounds of this invention are particularly useful are polystyrene, including impact polystyrene, ABS resin, SBR, polyisoprene, as well as natural rubber, polyesters including polyethylene terephthalate and polybutylene terephthalate, including copolymers, poly-alpha-olefins and lubricating oils such as those derived from mineral oil.

In general, polymers which can be stabilized include:

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyethylene or with polyisobutylene.

3. Copolymer of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/ethyl acrylate, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene norbornene.

4. Polystyrene.

5. Random copolymers of styrene or α-methylstyrene with dienes or acrylic derivatives, such as, for example, styrene/butadiene, styrene/acrylonitrile, styrene/alkyl methacrylates, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, polymers from halogen-containing vinyl compounds, as for example, polyvinyl chloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamides and polyacrylonitrile.

9. Copolymers from the monomers mentioned under (8) with each other or with other unsaturated monomers, such as, for instance, acrylonitrile/butadiene, acrylonitrile/alkyl acrylate or acrylonitrile/vinyl chloride copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer.

13. Polyphenylene oxides and sulfides.

14. Polyurethanes which are derived from polyethers, polyesters or polybutadienes with terminal hydroxyl groups on the one side and aliphatic or aromatic polyisocyanates on the other side, as well as precursors thereof.

15. Polyamides and copolyamides which are derived from diamines and dicarboxylic acid and/or from aminocarboxylic acids of the corresponding lactams, such as polyamide 4, polyamide 6, polyamide 6/6, polyamide 6/10, polyamide 11, polyamide 12, poly-2,4,4-trimethylhexamethylene terephthalamide or poly(m-phenylene isophthalamide), as well as copolymers thereof with polyethers, such as for instance, with polyethylene glycol, polypropylene glycol or polytetramethylene glycols.

16. Polyureas, polyimides and polyamide-imides.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block copolyether-esters derived from polyethers having hydroxyl end groups.

18. Polycarbonates.

19. Polysulfones and polyethersulfones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxy resins as crosslinking agents.

25. Crosslinked epoxide resins which are derived from polyepoxides, for example from bis-glycidyl ethers or from cycloaliphatic diepoxides and aromatic diepoxides.

26. Natural polymers, such as cellulose, rubber, gelatin and derivatives thereof which are chemically modified in a polymer-homolgous manner, such as cellulose acetates, cellulose propionates and cellulose butyrates, or the cellulose ethers, such as methyl cellulose.

27. Naturally occurring and synthetic organic materials which are pure monomeric compounds or mixtures of such compounds, for example mineral oils, animal and vegetable fats, oils and waxes, or oils, fats and waxes based on synthetic esters (e.g. phthalates, adipates, phosphates or trimellitates) and also mixtures of synthetic esters with mineral oils in any weight ratios, which materials may be used as plasticizer for polymers or as textile spinning oils, as well as aqueous emulsions of such materials.

28. Aqueous emulsions of natural or synthetic rubber, e.g. natural latex or latices of carboxylated styrene-/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tricyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethylenglycol-bis-[3,3-bis-(3-tert-butyl-4-hydroxyphenyl)butyrate]
di-(3-tert-butyl-4-hydroxy-5-methylphenyl)-dicyclopentadiene
di-[2-(3-tert-butyl-2-hydroxy-5-methyl-benzyl)-6-tert.butyl-4-methylphenyl] terephthalate.

1.5. Benzyl compounds, for example,
1,3,5-tri-(3,5-di-tert-butyl-4-hydroxybenzyl)-2,4,6-trimethylbenzene
bis-(3,5-di-tert-butyl-4-hydroxybenzyl) sulfide
3,5-di-tert-butyl-4-hydroxybenzylmercaptoacetic acid isooctyl ester
bis-(4-tert-butyl-3-hydroxy-2,6-dimethylbenzyl)dithiolterephthalate
1,3,5-tris-(3,5-di-tert.butyl-4-hydroxybenzyl) isocyanurate
1,3,5-tris-(4-tert.butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate

| 1.7. Esters of β-(3,5-di-tert-butyl-4-hydroxyphenyl)-propionic acid with monohydric or polyhydric alcohols, for example, | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

| 1.8. Ester of β-(5-tert-butyl-4-hydroxy-3-methylphenyl)-propionic acid with monohydric or polyhydric alcohols, for example, | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic diamide |

1.9. Amides of β-(3,5-di-tert-butyl-4-hydroxyphenyl)-propionic acid for example,
N,N'-bis-(3,5-di-tert-butyl-4-hydroxyphenylpropionyl)hexamethylenediamine
N,N'-bis-(3,5-di-tert-butyl-4-hydroxyphenylpropionyl)trimethylenediamine
N,N'-bis-(3,5-di-tert-butyl-4-hydroxyphenylpropionyl)hydrazine 2. UV absorbers and light stabilisers 2.1. 2-(2'-Hydroxyphenyl)-benztriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octyloxy, 3',5'-di-tert-amyl-, 3',5'-bis-(α,α-dimethylbenzyl)-derivative.

2.2. 2-Hydroxy-benzophenones, for example, the 4-hydroxy-, 4-methoxy-, 4-octyloxy, 4-decyloxy-, 4-dodecyloxy-, 4-benzyloxy, 4,2',4'-trihydroxy- and 2'-hydroxy-4,4'-dimethoxy derivative.

2.3. Ester of optionally substituted benzoic acids for example, phenyl salicylate, 4-tert-butylphenyl salicylate, octylphenyl salicylate, dibenzoylresorcinol, bis-(4-tertbutylbenzoyl)-resorcinol, benzoylresorcinol, 3,5-di-tertbutyl-4-hydroxybenzoic acid 2,4-di-tert-butyl-phenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methylindoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)sebacate, bis-(1,2,2,6,6-pentamethylpiperidyl)sebacate, n-butyl-3,5-di-tert-butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert.octylamino-2,6-dichloro-1,3,5-s-triazine, tris-(2,2,6,6-tetramethylpiperidyl)nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearylpentaerythrityl diphosphite, tris-(2,4-di-tert-butylphenyl)-phosphite, diisodecylpentaerythrityl diphosphite, di-(2,4-di-tert-butylphenyl)pentaerythrityl diphosphite, tristearyl-sorbityl triphosphite, tetrakis-(2,4-di-tert-butylphenyl)-4,4'-diphenylylendiphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrityl-tetrakis (β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert-butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticizers, lubricants, emulsifiers, pigments, optical brighteners, flame-proofing agents, antistatic agents, blowing agents and thiosynergists such as dilauryl thiodipropionate or distearyl thiodipropionate.

As previously noted, a number of the compounds falling within the scope of formula I have been disclosed in the cited publications. Other compounds are novel, however, and thus comprise part of the instant invention. These novel compounds correspond to those of formula I where $R_1$ is hydrogen, and $R_2$ is cyclohexyl, cyclohex-3-enyl or 3,5-di-tert-butyl-4-hydroxyphenyl. These new compounds are, of course, prepared in the manner described hereinabove.

The following examples further illustrate the embodiments of this invention. In these examples, all parts given are by weight unless otherwise specified.

EXAMPLE 1

2,2-Bis(3,5-di-tert-butyl-4-hydroxyphenylthio)octane

A flask under a nitrogen atmosphere is charged with a solution of 23.84 grams of 2,6-di-tert-butyl-4-mercaptophenol and 6.41 grams of 2-octanone in 150 ml of methyl alcohol. The solution is then treated with anhydrous hydrogen chloride and held at 55° C. for two hours. The resulting precipitate is filtered off and dried to give 23.75 grams (81% yield) of white solid, mp 130°–133° C.

Calcd. for $C_{36}H_{58}O_2S_2$: C, 73.7; H, 10.0. Found: C, 74.0; H, 9.8.

EXAMPLE 2

1,1-Bis(3,5-di-tert-butyl-4-hydroxyphenylthio)-1-(3,5-di-tert-butyl-4-hydroxyphenyl)methane The procedure of Example 1 is repeated using 23.84 grams of 2,6-di-tert-butyl-4-mercaptophenol, 11.72 grams of 3,5-di-tert-butyl-4-hydroxybenzaldehyde and 150 ml of methyl alcohol. Trituration with methyl alcohol gives 30 grams (87% yield) of white crystals, mp 175°–177° C.

Anal. Calcd. for $C_{43}H_{64}O_3S_2$: C, 74.5; H, 9.3; S, 9.3. Found: C, 74.5; H, 9.3; S, 9.5.

EXAMPLE 3

4,4-Bis(3,5-di-tert-butyl-4-hydroxyphenylthio)-2,6,8-trimethylnonane

The procedure of Example 1 is repeated using 9.22 grams of 2,6,8-trimethylnonan-4-one, 23.84 grams of 2,6-di-tert-butyl-4-mercaptophenol, and 150 ml of methyl alcohol. The product is purified by flask chromatography to give a clear syrup whose proton NMR spectrum is consistent with the desired structure.

EXAMPLE 4

α,α-Bis(3,5-di-tert-butyl-4-hydroxyphenylthio)toluene

The procedure of Example 1 is repeated using 23.84 grams of 2,6-di-tert-butyl-4-mercaptophenol, 5.31 grams of benzaldehyde, and 150 ml of methyl alcohol. The product is triturated with methyl alcohol to give 18.74 grams (66% yield) of white crystals, mp 122°–124° C.

Anal. Calcd. for $C_{35}H_{48}O_2S_2$: C, 74.4; H, 8.6. Found: C, 74.1; H, 8.6.

EXAMPLE 5

1,1-Bis(3,5-di-tert-butyl-4-hydroxyphenylthio)-2-ethylhexane

The procedure of Example 1 is repeated using 23.84 grams of 2,6-di-tert-butyl-4-mercaptophenol, 6.41 grams of 2-ethylhexanal, and 150 ml of methyl alcohol. The product is purified by dry-column chromatography to give 10.29 grams of a clear syrup.

Anal. Calcd. for $C_{35}H_{48}O_2S_2$: C, 73.7; H, 10.0. Found: C, 73.9; H, 9.9.

EXAMPLE 6

1,1-Bis(3,5-di-tert-butyl-4-hydroxyphenylthio)cyclohexane

The procedure of Example 1 was repeated using 28.71 grams of 2.6-di-tert-butyl-4-mercaptophenol, 5.91 grams of cyclohexanone, and 150 ml of methyl alcohol. The product is triturated with methyl alcohol to give 31.17 grams (93.3% yield) of white solid, mp 195°–197° C.

Anal. Calcd. for $C_{34}H_{52}O_2S_2$: C, 73.3; H, 9.4. Found: C, 73.4; H, 9.5.

EXAMPLE 7

1,1-Bis(3,5-di-tert-butyl-4-hydroxyphenylthio)-1-(cyclohex-3-enyl)methane

A solution of 10 grams of 2,6-di-tert-butyl-4-mercaptophenol and 2.3 grams of cyclohex-3-enyl carboxaldehyde is charged to a flame-dried flask and treated with 1.0 ml of tetrafluoroboric acid and stirred for two hours. The reaction mixture is extracted with aqueous sodium bicarbonate and dried over anhydrous magnesium sulfate. The solvent is stripped in vacuo, and the residue recrystallized from acetonitrile to give 9.0 grams (76% yield) of white crystals, mp 122°–125° C.

Anal. Calcd. for $C_{35}H_{52}O_2S_2$: C, 73.9; H, 9.2; S, 11.3. Found: C, 73.9; H, 9.3; S, 11.2.

EXAMPLE 8

This example illustrates the stabilizing effectiveness of the instant stabilizers in impact polystyrene (IPS).

In the laboratory procedure utilized herein, a solution of eight weight percent polybutadiene rubber (Firestone—DIENE 55) dissolved in styrene monomer is prepared on a roller mill. The indicated amount of stabilizer is also introduced at this point. 500 ppm of zinc stearate is added to aid in removing the sample from the bottle after the polymerization. The bottle is screwed into the polymerization apparatus which is equipped with a double helical ribbon stirrer. Since most commercial IPS bulk polymerizations are thermally initiated processes, no initiator is used in the laboratory process. A nitrogen atmosphere is established and the reactor is then heated to 121° C. within ½ hour. Heating continue at 121° C. with efficient stirring until there is a 30 to 35% monomer conversion (ca. 2.5 hours). The stirring rate is controlled to yield a two to four micron rubber particle size. The bottles are removed from the polymerization apparatus, blanketed with nitrogen, capped, and then placed in a fluidized bed sand bath to complete the polymerization. The bottles are heated in the bath in the following fashion: one hour at 100° C. to equilibrate the temperature, one hour to reach 140° C. and then an additional eight hours with the temperature increasing at the rate of 10° C. per hour to a maximum of 220° C. After the resin is cooled, the bottle is broken and the glass is removed. The average weight of the polymer block is slightly over 600 grams. The block is then placed into a vacuum oven at 200° C. and a vacuum of 1 mm applied as the polymer is heated for 45 minutes in order to remove all volatiles. The block is removed from the oven, immediately placed in a heated (205° C.) hydraulic press and then pressed into a thick slab between two sheets of aluminum foil (three minutes heating, five minutes in a cold press). The slab is split with a band saw and the pieces are granulated.

All batches were extruded at 205° C. and then pelletized. The pellets are compression molded at 205° C. into 125 mil (3.175 mm) tensile bars. The bars are then aged at 150° C. on glass plates placed on rotating shelves in a forced air oven. Other tensile bars are aged at 80° C. suspended from rotating shelves in a forced air oven. The specimen yellowness index is determined on the bars at various intervals according to ASTM D-1925-63T. Correspondingly, the bars are periodically measured for percent elongation into the Instron Tensile Testing Apparatus (Instron Engineering Corporation, Massachusetts) at a pull rate of 5 mm/minute according to ASTM D638.

| | Oven Aged Samples at 80° C. | | | | | |
|---|---|---|---|---|---|---|
| | Conc. (% | % Elongation (Hours at 80° C.) | | | | |
| Additive | by wt.) | 0 | 300 | 600 | 900 | 1200 |
| None | — | 33 | 9 | 3 | 3 | 3 |
| Compound of Example 1 | 0.1 | 55 | 24 | 10 | 9 | 7 |
| Compound of Example 7 | 0.1 | 49 | 29 | 10 | 8 | 5 |

| Additive | Conc. (% by wt.) | Yellowness Index | | | | |
|---|---|---|---|---|---|---|
| None | — | 7 | 14 | 45 | 59 | — |
| Compound of Example 1 | 0.1 | 0 | 16 | 27 | 38 | 52 |
| Compound of Example 7 | 0.1 | 2 | 8 | 19 | 31 | 43 |

Oven Aged Samples at 150° C.

| Additive | Conc. (% by wt.) | % Elongation (Hours at 150° C.) | | | | |
|---|---|---|---|---|---|---|
| | | 0 | ½ | 1 | 1½ | 2 |
| None | — | 33 | 7 | 7 | 3 | 3 |
| Compound of Example 1 | 0.1 | 55 | 50 | 19 | 8 | 7 |
| Compound of Example 7 | 0.1 | 49 | 36 | 18 | 10 | 7 |
| | | Yellowness Index | | | | |
| None | — | 7 | 18 | 30 | 38 | 43 |
| Compound of Example 1 | 0.1 | 0 | 5 | 7 | 10 | 15 |
| Compound of Example 7 | 0.1 | 2 | 5 | 9 | 10 | 14 |

EXAMPLE 9

Unstabilized polypropylene powder (Hercules Profax 6501) is thoroughly blended with 0.2%, by weight, of additive. The blended materials are then milled on a two roll mill at 182° C. for 5 minutes, after which time the stabilized polypropylene is sheeted from the mill and allowed to cool. The milled polypropylene is then cut into pieces and compression molded on a hydraulic press at 220° C. at 175 psi (12.3 Kg/cm$^2$) into 5 mil (0.127 mm) films. The samples are exposed to a fluorescent suinlight/black light chamber until failure. Failure is determined as the time when the films show the first signs of decomposition (e.g. cracking or brown edges).

| Additive | Hours to Failure |
|---|---|
| None | 200–300 |
| Compound of Example 1 | 430 |
| Compound of Example 2 | 460 |
| Compound of Example 4 | 380 |
| Compound of Example 6 | 480 |
| Compound of Example 7 | 500 |

EXAMPLE 10

The oxidation stability of milled polypropylene containing, respectively, 0.2%, by weight, of the instant additives as well as of a synergized formulation containing 0.1%, by weight, of the additive in the presence of 0.3%, by weight, distearyl thiodipropionate (DSTDP) on plaques of 25 mil (0.635 mm) thickness is determined by exposing said plaques to air in a forced draft oven at 150° C. The plaques are considered to have failed on showing the first signs of decomposition (e.g. cracking or brown edges).

| Additive Compound of | Time to Failure (Hrs) | |
|---|---|---|
| | Additive Conc. 0.2% by wt | Synergized Composition (% by wt) 0.1% Additive + 0.3% DSTDP |
| Base Resin (0.3% DSTDP) | <20 | <20 |
| Example 1 | 20 | 80 |
| Example 2 | 30 | 160 |
| Example 4 | 50 | 220 |
| Example 6 | 20 | 280 |
| Example 7 | 120 | 180 |

Examples 8–10 thus indicate the superior stabilizing performance of the instant compounds in several substrates compared to the base resin in the absence of a compound of this invention.

Summarizing, it is seen that this invention provides a group of compounds having superior stabilizing activity in a variety of organic materials. Variations may be made in proportions, procedures and materials without departing from the scope of the invention as defined by the following claims.

What is claimed is:

1. A composition of matter comprising an organic material subject to oxidative, thermal or photo-degradation stabilized with an effective stabilizing amount of a compound of formula I

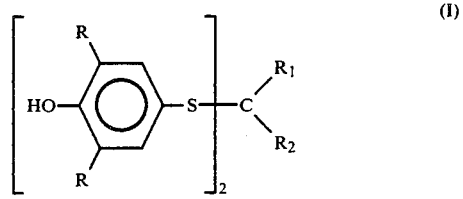

wherein
R is tert-butyl,
R$_1$ is hydrogen or a straight- or branched-chain alkyl of 1 to 4 carbon atoms,
R$_2$ is a straight- or branched-chain alkyl of 1 to 17 carbon atoms or cyclohex-3-enyl; where R$_1$ and R$_2$ together must have a total of at least 5 carbon atoms.

2. A composition according to claim 1, wherein the organic material is a synthetic polymer.

3. A composition according to claim 2, wherein said synthetic polymer is a polyolefin homopolymer or copolymer.

4. A composition according to claim 1, wherein the organic materal is selected from the group consisting of polystyrene, acrylonitrile/butadiene styrene, styrene/butadiene rubber, natural rubber and polyesters.

5. A composition according to claim 1 where in the compound of formula I, R$_1$ is hydrogen or methyl, R$_2$ is alkyl of 6 to 8 carbon atoms.

6. A composition according to claim 1 wherein the compound of formula I is 2,2-bis(3,5-di-tert-butyl-4-hydroxyphenylthio)octane.

7. A composition according to claim 1 wherein the compound of formula I is 1,1-bis(3,5-di-tert-butyl-4-hydroxyphenylthio)1-cyclohex-3-enyl)methane.

8. A composition according to claim 1 containing 0.01 to 5% by weight, based on the stabilized composition, of a compound of formula I.

9. A method of stabilizing an organic material against oxidative, thermal or photo-degradation which comprises incorporating into said organic material an effective stabilizing amount of a compound as defined in claim 1.

10. The compound of the formula

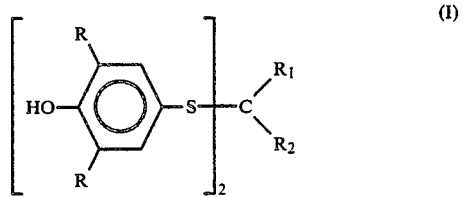

wherein R is tert-butyl,
R$_1$ is hydrogen, and
R$_2$ is cyclohex-3-enyl.

* * * * *